United States Patent
Hierzer

(10) Patent No.: US 9,757,618 B2
(45) Date of Patent: Sep. 12, 2017

(54) TRAINING DEVICE, SYSTEM AND METHOD FOR MONITORING A PHYSICAL EXERCISE

(71) Applicant: H4X e.U., Graz (AU)

(72) Inventor: Andreas Hierzer, Graz (AU)

(73) Assignee: H4X e.U., Graz (AU)

( * ) Notice: Subject to any disclaimer, the term of this patent is extended or adjusted under 35 U.S.C. 154(b) by 0 days.

(21) Appl. No.: 14/951,725

(22) Filed: Nov. 25, 2015

(65) Prior Publication Data
US 2017/0028257 A1 Feb. 2, 2017

(30) Foreign Application Priority Data

Jul. 29, 2015 (DE) .......................... 10 2015 214 394

(51) Int. Cl.
A63B 24/00 (2006.01)
A63B 21/00 (2006.01)
(Continued)

(52) U.S. Cl.
CPC ...... *A63B 24/0062* (2013.01); *A63B 21/0023* (2013.01); *A63B 21/4037* (2015.10); *A63B 23/0205* (2013.01); *A63B 24/0087* (2013.01); *A63B 71/0619* (2013.01); *G06F 19/3481* (2013.01); *G06K 9/00342* (2013.01); *A63B 21/00047* (2013.01); *A63B 23/0211* (2013.01); *A63B 23/0233* (2013.01); *A63B 71/0622* (2013.01); *A63B 2024/0068* (2013.01); *A63B 2071/0625* (2013.01); *A63B 2071/0655* (2013.01); *A63B 2207/02* (2013.01); *A63B 2220/51* (2013.01); *A63B 2220/56* (2013.01);
(Continued)

(58) Field of Classification Search
CPC . A63B 24/00; A63B 24/0062; A63B 24/0087; A63B 21/4037; A63B 21/0023; A63B 21/00047; A63B 23/0205; A63B 23/0233; A63B 71/0619; A63B 71/0622; A63B 2071/0655; A63B 2071/0625; A63B 2225/50; A63B 2225/62
See application file for complete search history.

(56) References Cited

U.S. PATENT DOCUMENTS 6,468,211 B1 * 10/2002 Binder .................. A61B 5/083
482/7
9,522,317 B2 * 12/2016 Bleich ................ A63B 71/0686
(Continued)

FOREIGN PATENT DOCUMENTS

DE 102013202878 A1 9/2014
EP 1890779 B1 2/2008

*Primary Examiner* — Glenn Richman
(74) *Attorney, Agent, or Firm* — Millen, White, Zelano & Branigan, P.C.; William Nixon

(57) ABSTRACT

A training device for monitoring a physical exercise is formed having a volume element, a sensor apparatus which is designed to detect a mechanical force and/or a pressure which a user exerts on the volume element while performing the physical exercise, and to generate a measurement signal on the basis of the detected force and/or the detected pressure, and an evaluation apparatus which is designed to compare the measurement signal generated by the sensor apparatus with a value range and/or a target value and to automatically generate an output signal on the basis of the result of the comparison.

9 Claims, 7 Drawing Sheets

(51) Int. Cl.
    *A63B 21/002* (2006.01)
    *A63B 23/02* (2006.01)
    *A63B 71/06* (2006.01)
    *G06F 19/00* (2011.01)
    *G06K 9/00* (2006.01)

(52) U.S. Cl.
    CPC ....... *A63B 2225/50* (2013.01); *A63B 2225/62* (2013.01)

(56) References Cited

U.S. PATENT DOCUMENTS

| | | | |
|---|---|---|---|
| 2005/0256421 A1* | 11/2005 | Bryant | A61B 5/087 |
| | | | 600/538 |
| 2008/0189827 A1 | 8/2008 | Bauer | |
| 2010/0121211 A1* | 5/2010 | Bryant | A61B 5/087 |
| | | | 600/538 |
| 2015/0080746 A1* | 3/2015 | Bleich | A63B 71/0686 |
| | | | 600/479 |
| 2016/0220869 A1* | 8/2016 | McBride | A63B 26/003 |

* cited by examiner

TRAINING DEVICE, SYSTEM AND METHOD FOR MONITORING A PHYSICAL EXERCISE

FIELD OF THE INVENTION

The present invention relates to a training device, to a system, and to a method for monitoring a physical exercise, in particular a medical exercise, for example a sports medicine exercise.

BACKGROUND

In some types of medical exercises, a patient is instructed to tense a particular muscle or a particular muscle group in a certain manner while performing the exercise. During the exercise, the patient is additionally supposed to exert a predetermined pressure or a predetermined force onto a measurement apparatus by tensing the muscle or muscle group. The pressure or the force should be kept within a predetermined value range. The exercise is only performed effectively when this is the case, and at best can be useless when this is not the case, in other words, when the exerted force or the exerted pressure is outside the predetermined value range.

For physical exercises of this type, use is typically made of a blood pressure measurement device which comprises a sleeve and a pressure gauge and which the patient as the user straps on or wedges between himself and a wall or the floor. With the aid of the pressure gauge, the user or a supervisor has to assess the force or pressure exerted during the physical exercise. The disadvantage is that the user himself thus not only has to focus on performing the physical exercise correctly, but also has to keep an eye on the pressure gauge and at the same time perform a calculation as to whether or not the current indication shows that the user is exerting a sufficient force or a sufficient pressure. The user is also faced with the problem that the sleeve of the blood pressure measurement device could have been pumped up by different amounts at the start of the exercise, which results in inaccuracies in said user's calculations. With some exercises, the additional handling of the blood pressure measurement device can be cumbersome or impossible.

Therefore, there is a need for a robust training device for monitoring a physical exercise which is simple to operate and clearly displays to the user whether or not he is performing the exercise to be performed in the correct manner.

SUMMARY OF THE INVENTION

Accordingly, a training device for monitoring a physical exercise is provided, which comprises a volume element, a sensor apparatus and an evaluation apparatus. The sensor apparatus is designed to detect a mechanical force which a user exerts on the volume element while performing the physical exercise. Alternatively or additionally, the sensor apparatus can be designed to detect a pressure which a user exerts on the volume element while performing the physical exercise. The sensor apparatus is designed to generate a measurement signal on the basis of the detected force and/or the detected pressure.

The volume element is to be understood in particular as being an object having a non-negligible extension in three spatial dimensions. The volume element is preferably resilient and not brittle.

The evaluation apparatus is designed to compare the measurement signal generated by the sensor apparatus with a value range and/or a target value and to automatically generate an output signal on the basis of the result of the comparison.

The value range can be a predetermined value range which, for example, is stored in the evaluation apparatus. The value range can be divided into a target value, for example right in the middle of the value range, and, for example, tolerance ranges to either side of said target value. Alternatively or additionally, the value range and/or the target value can be able to be input and/or adjusted by the user or by a third party, for example by means of a smartphone.

A system for monitoring a physical exercise is also provided, which comprises a volume element, a sensor apparatus and an interface apparatus. The sensor apparatus is designed to detect a mechanical force and/or a pressure which a user exerts on the volume element while performing the physical exercise, and to generate a measurement signal on the basis of the detected force and/or the detected pressure.

The interface apparatus is designed to transmit the generated measurement signal to a terminal of the system. The volume element, the sensor apparatus and the interface apparatus are integrated in a training device. The terminal is separate from the training device.

The terminal comprises an evaluation unit. The evaluation unit is designed to compare the measurement signal generated by the sensor apparatus with a value range, to automatically generate an output signal on the basis of the result of the comparison and to transmit this signal to an output unit. The output unit is designed to output an optical and/or acoustic and/or haptic information signal to the user on the basis of the output signal generated by the evaluation unit. The output unit can be included in either the terminal or the training device.

A method for monitoring a physical exercise is also provided, said method comprising the steps of: detecting a mechanical force and/or a pressure which a user exerts on a volume element while performing a physical exercise; generating a measurement signal on the basis of the detected force and/or the detected pressure; and generating an output signal on the basis of a comparison of the generated measurement signal with a value range and/or a target value.

As described above, the physical exercise to be performed can in particular be understood to be a medical exercise, for example from the sports medicine field. In particular, the exercise can be an exercise for strengthening a muscle, preferably an abdominal muscle and/or a back muscle.

The present invention creates a possibility of monitoring a physical exercise which is particularly user-friendly and which provides the user with information, in a particularly simple and quick manner, as to whether the pressure exerted on the volume element by the user or the mechanical force exerted on the volume element by the user is sufficient for the physical exercise to be performed.

The automatic evaluation of the generated measurement signal compared with the value range relieves the user of the sometimes complicated calculation, which may include a large number of factors. In addition, numerous measurement inaccuracies are avoided.

Additional advantages and advantageous embodiments and developments can be found in the dependent claims and in the description with reference to the drawings.

According to one development, the sensor apparatus is designed to detect the mechanical force and/or the pressure continuously or at regular intervals and to generate the measurement signal based thereon continuously or at regular intervals. The evaluation apparatus can be designed to automatically adjust the generated output signal continuously to the continuously generated measurement signal, or to automatically adjust said generated output signal at regular intervals to the measurement signal which is generated at regular intervals. The output signal can thus be kept current at all times so that the user is immediately able to adjust his performance of the exercise if the output signal indicates that the pressure or force said user is exerting on the volume element is too high or too low.

According to another development, the volume element is formed as a cushion which is filled with a gas, in particular air, or can be filled with a gas, in particular air. The sensor apparatus can comprise a pressure sensor which is designed to detect an internal pressure in the cushion and to generate the measurement signal on the basis of the detected internal pressure. The training device can thus fulfil its function relatively independently, in particular completely independently, of where and how the user exerts the pressure or the mechanical force on the volume element. A predetermined initial internal pressure can be applied to the cushion, which pressure is selected such that the pressure sensor can detect pressure changes from the initial internal pressure in a particularly precise manner. The initial internal pressure can also be selected such that the cushion to which the initial internal pressure has been applied has a flexibility and/or resilience which is pleasant for the user and advantageous in medical terms.

According to another development, the training device comprises an internal output apparatus which is designed to automatically output an optical and/or acoustic and/or haptic information signal to the user on the basis of the generated output signal. This makes it possible for the user to be aware of the information signal even if he is not able to see an optical display fixed to the training device, for example, owing to the exercises to be performed for example. The optical information signal can in particular be output by lights of an illumination apparatus having a predetermined brightness and/or colour, so that the user is aware of the optical information signal even when he is not currently looking directly at the illumination apparatus.

According to another development, the internal output device is designed to adjust a wavelength of the optical information signal to be output, on the basis of the output signal. In particular, the output signal can contain information as to how the force currently being exerted on the volume element by the user or the pressure currently being exerted deviates from the corresponding value range and/or a target value. The wavelength of the optical information signal to be output, i.e. a wavelength of emitted light as an optical information signal, can be adjusted in accordance with a constant function of a difference between the force currently being exerted or the pressure currently being exerted and the value range or the target value. The wavelength can in particular be adjusted either proportionally or indirectly proportionally to the aforementioned difference. For example, the emitted light, which is always within the visible spectrum, can have a wavelength which becomes smaller the further the exerted force or the exerted pressure is below the predetermined value range or the target value, and can be designed to have a wavelength which becomes longer the further the exerted force or the exerted pressure is above the predetermined value range or target value. If the exerted force or the exerted pressure is within the value range, the optical information signal can be emitted e.g. with a wavelength in the yellow colour range, for example from 560 to 580 nm.

According to another development, the internal output apparatus is designed to adjust a frequency of an acoustic information signal to be output, on the basis of the output signal. This can occur as described above in relation to the optical information signal, although, instead of the wavelength of light in the form of an optical information signal, a frequency of a sound in the form of an acoustic information signal to be output is adjusted according to a difference between the exerted force or the exerted pressure and the value range or a target value. For example, a higher sound signal can be emitted the more pressure or force is exerted on the volume element and a lower sound signal can be emitted the less force or pressure is exerted on the volume element. When the force or pressure is within the value range, in particular in a narrow range around a target value, a sound of for example 440 Hz can be emitted.

According to another development, the internal output apparatus can be designed to adjust a characteristic of a haptic information signal on the basis of the output signal. A characteristic of the haptic information signal is to be understood in particular as a frequency and/or an amplitude with which a vibrating element of the internal output apparatus vibrates in order to output the haptic information signal to the user. The frequency and/or amplitude of the vibrating element can be adjusted similarly to the frequency of the acoustic information signal, as described above.

According to another development, the training device comprises an exercise mat in which at least the volume element and the sensor apparatus are integrated. Other apparatuses or elements of the training device can also be integrated in the exercise mat. The training device as a whole can also be formed as an exercise mat comprising integrated elements and apparatuses, in other words all the features of the training device (apart from the exercise mat) are integrated in the exercise mat. Therefore, the training device is both particularly easy to handle and compact. In addition, all the apparatuses of the training device can be adjusted specifically to the exercise mat, as a result of which measurement inaccuracies during the detection of the exerted force and/or the exerted pressure can be reduced.

According to another development, the training device comprises an interface apparatus, by means of which the generated output signal can be transmitted to an external terminal. The external terminal can be designed to automatically output an optical and/or acoustic and/or haptic information signal to the user on the basis of the received output signal, in a similar manner to the internal output apparatus. The external terminal can also be designed to adjust a wavelength of the optical information signal to be output and/or a frequency of the acoustic information signal to be output and/or a characteristic of the haptic information signal to be output, on the basis of the output signal. It is thus possible to output an information signal which can be perceived particularly effectively by the user since the user can place the external terminal separately from the training device. Furthermore, a plurality of training devices, which, for example, can each be specifically adapted to one or more physical exercises to be performed, can use the same external terminal to output the information signal. As a result, technical complexity and costs can be reduced for the user.

According to another development, a system for monitoring a physical exercise is provided, which comprises a training device according to the invention, in which at least the volume element, the sensor apparatus, the evaluation apparatus and the interface apparatus are integrated. The system further comprises a terminal which is separate from the training device and comprises an output unit which is designed to output an optical and/or acoustic and/or haptic information signal to the user on the basis of the output signal generated by the evaluation apparatus.

BRIEF DESCRIPTION OF THE DRAWINGS

The present invention will be described in more detail below on the basis of the embodiments shown in the schematic figures of the drawings, in which.

Figure 1:
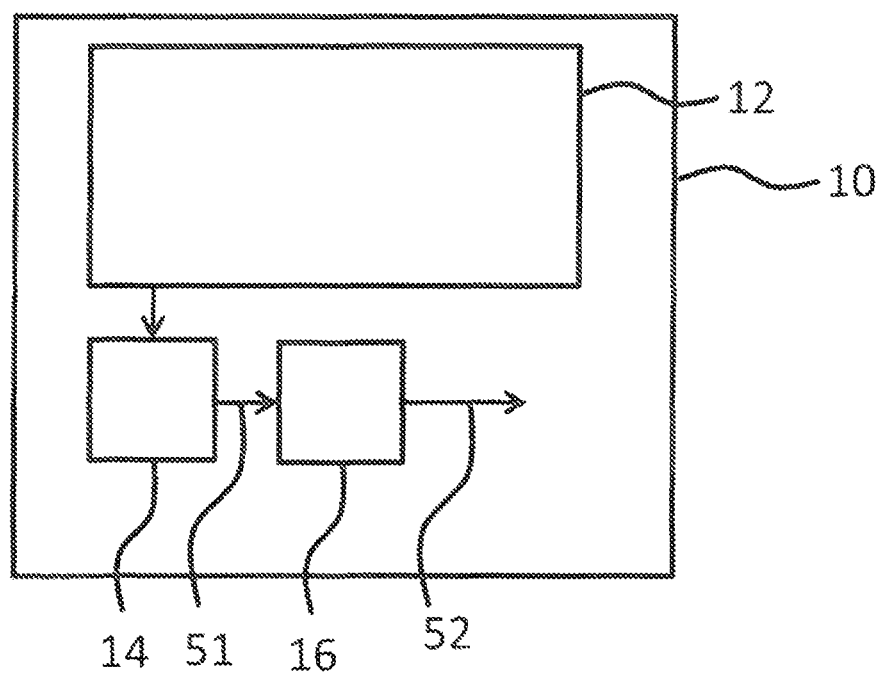
FIG. 1 is a schematic block diagram of a training device for monitoring a physical exercise according to an embodiment of the present invention.

In all the figures, unless indicated otherwise, like elements and apparatuses or those with the same function are provided with the same reference numeral. The numbering of method steps is intended to improve clarity and, unless indicated otherwise, is especially not intended to imply a particular time sequence. A plurality of method steps can also be carried out at the same time.

DETAILED DESCRIPTION OF SOME OF THE EMBODIMENTS OF THE INVENTION

FIG. 1 is a schematic block diagram of a training device 10 for monitoring a physical exercise according to an embodiment of the present invention.

The training device 10 comprises a volume element 12 and a sensor apparatus 14 which is designed to detect a mechanical force and/or a pressure which a user exerts on the volume element 12 while performing the physical exercise, and which is also designed to generate a measurement signal 51 on the basis of the detected force and/or the detected pressure.

In this case, the volume element can, for example, have a width of more than 10, preferably of more than 20, more preferably of more than 50 cm, and a length of more than 10 cm, preferably of more than 30 cm, more preferably of more than 50 cm.

The training device 10 further comprises an evaluation apparatus 16 which is designed to compare the measurement signal 51 generated by the sensor apparatus 14 with a value range and/or a target value, in particular a value range and/or target value which is predetermined for the physical exercise, and to automatically generate an output signal 52 on the basis of the result of the comparison. The output signal 52 can be processed within the training device 10 or transmitted to an external terminal, for example a smartphone or tablet.

If the training device 10 is designed such that an electric current is needed, said current can, for example, be provided by connecting the training device 10 to a domestic mains supply. Alternatively or additionally, the training device 10 can comprise an internal electrical energy store, for example a battery or an accumulator.

Figure 2:
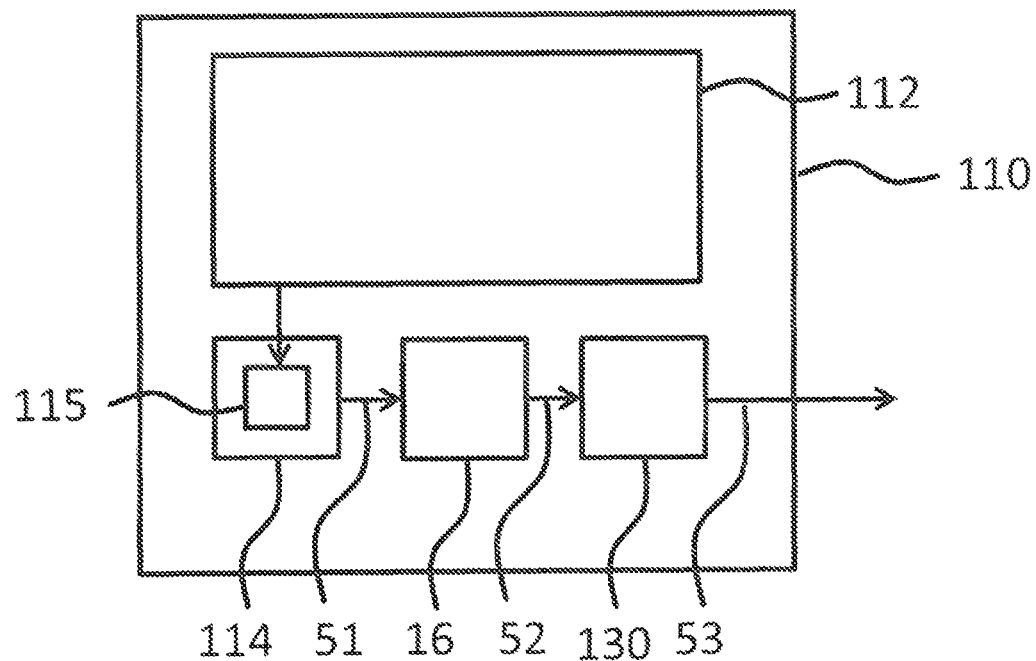
FIG. 2 is a schematic block diagram of a training device according to a further embodiment of the present invention.

FIG. 2 is a schematic block diagram of a training device 110 according to a further embodiment of the present invention.

The training device 110 is a variant of the training device 10 that differs from the training device 10 on account of the design of the volume element 112, the sensor apparatus 114 and an internal output apparatus 130.

The volume element 112 preferably comprises a textile and/or a plastics material or consists of a textile and/or a plastics material. In particular, the volume element 112 can be formed as a single-piece plastics part or as an assembly of at least two plastics parts. The plastics material can, for example, be an elastomer or a thermoplastic. For example, the plastics material can be rubber or a foam or can comprise these materials. The foam can, for example, be polyethylene foam or a foam consisting of ethylene copolymer. In general, use can be made of any plastics material that is used for commercially available exercise mats such as gymnastics mats, fitness mats and yoga mats.

The volume element 112 can comprise a first surface on which the user either indirectly or directly exerts the mechanical force and/or the pressure when performing the physical exercise by, for example, placing himself on the volume element 112 or on a part of the volume element 112. The volume element 112 can comprise a second surface which faces away from the first surface and on which a pressure sensor 115 of the sensor apparatus 114 of the training device 110 is formed. The pressure sensor 115 is designed to detect a force or a pressure which the volume element 112 exerts on the pressure sensor 115. The sensor apparatus 114 is designed to detect the force, which the user exerts on the volume element 112 while performing the physical exercise and from which the force detected by the pressure sensor 115 resulted, on the basis of the force detected by the pressure sensor 115. The pressure sensor 115 can, for example, be a piezoresistive pressure sensor, a piezoelectric pressure sensor or the like. The sensor apparatus 114 can in particular be designed or calibrated to disregard the force exerted on the pressure sensor 115 by the volume element 112 as a result of the weight of the volume element 112 itself.

The training device 110 further comprises an internal output apparatus 130 which is designed to receive the generated output signal 52 and, on this basis, to output an information signal 53 to the user, in particular continuously or at regular intervals. The output apparatus 130 can comprise a speaker for outputting an acoustic information signal, an illumination apparatus for outputting an optical information signal and/or a vibration element for outputting a haptic information signal. For example, the illumination apparatus can comprise light-emitting diodes (LEDs).

For example, a regular beep can be output by the speaker of the output apparatus 130, the tone frequency of which is continuous but the repetition frequency of which increases or decreases according to the output signal depending on the extent to which the pressure currently being exerted on the volume element 112 or the force currently being exerted on the volume element 112 exceeds or falls short of the value range, in particular the target value.

Figure 3:
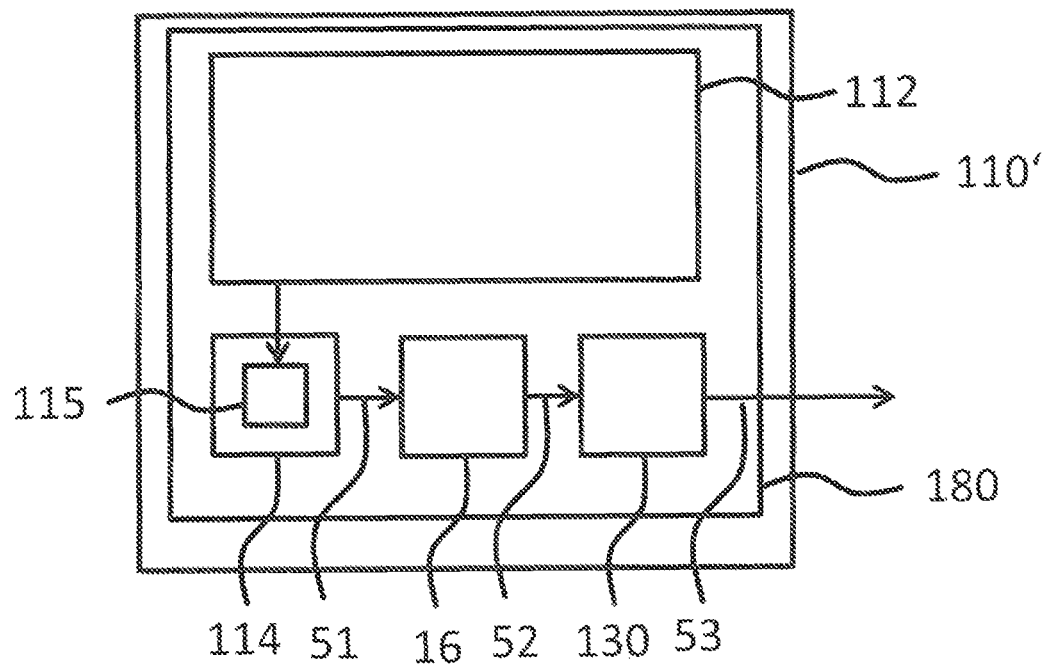
FIG. 3 is a schematic block diagram of a training device according to another further embodiment of the present invention.

FIG. 3 is a schematic block diagram of a training device 110' according to another further embodiment of the present invention. The training device 110' is a variant of the training device 110 and only differs therefrom in that the training device 110' is integrated as a whole in an exercise mat 180 of the training device 110'.

An exercise mat should in particular be understood to be a fitness mat, a yoga mat or any other sports mat. In this case, the exercise mat can have a width of more than 10, preferably of more than 20, more preferably of more than 50 cm for example, and a length of more than 10 cm, preferably of more than 30 cm, more preferably of more than 100 cm.

The exercise mat 180 can have a bearing side which is designed to be placed onto a floor, and an exercise side which is designed for physical exercises to be performed thereon. The volume element 112 can be integrated in the exercise mat 180 on the exercise side so that said element is visible to the user as a cushion-like raised region in the exercise surface, while at the same time the exercise mat 180 can rest flat on the ground by means of the bearing side. The training device 110' can, for example, be advantageously used for exercises for training abdominal or back muscles, in particular deep abdominal or back muscles.

Figure 4:
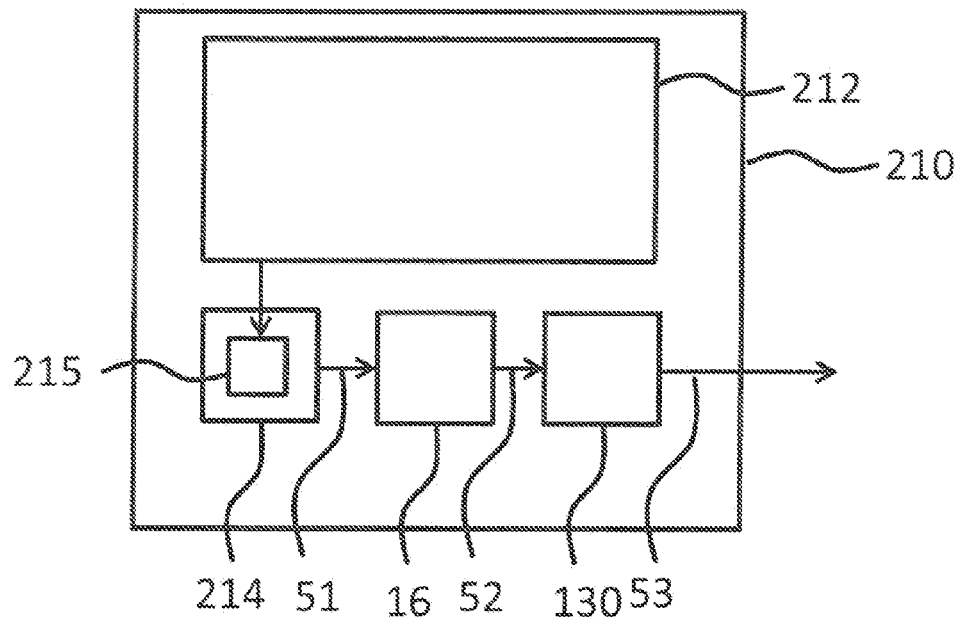
FIG. 4 is a schematic block diagram of a training device according to another further embodiment of the present invention.

FIG. 4 is a schematic block diagram of a training device 210 according to another further embodiment of the present invention. The training device 210 is a variant of the training device 110 that differs therefrom on account of the design of both the volume element 212 and the sensor apparatus 214 of the training device 210.

The volume element 212 is formed as a cushion 212 which is filled with air or can be filled with air. The volume element 212 can comprise an optional filling apparatus. In a simple case, the filling apparatus can be formed as an air valve like the valve in an air bed, by means of which the volume element 212 can be pumped up by means of an air pump, in other words an internal pressure can be applied thereto. Alternatively or additionally, the filling apparatus can also be formed having an integrated air pump which can be used to pump up the volume element 212. Alternatively or additionally, the filling apparatus can have a self-inflation apparatus which is designed to automatically apply a predetermined initial internal pressure to the volume element 212 when a valve in the self-inflation apparatus is opened.

The sensor apparatus 214 of the training device 210 has a pressure sensor 215 which is designed to detect an internal pressure in the cushion 212 and to generate the measurement signal 51 on the basis of the detected internal pressure in the cushion 212. The pressure sensor 215 can, for example, be integrated in the filling apparatus. Advantageously, the pressure sensor 215 is coupled to the optional self-inflation apparatus, the pressure sensor 215 of the self-inflation apparatus being designed to provide information as to whether the initial internal pressure has already been reached or exceeded.

The training device 210 comprising the inflatable volume element 212 can be particularly compact since the user can reduce the volume of a training device 210 which is not currently being used by letting out the air from the cushion 212 and thus store said device away in a compact manner. If the filling apparatus is designed such that the user manually pumps up the cushion 212, it can be provided for the training device 210 to be able to be transferred into a pumping mode in which the information signal 53 displays whether the initial internal pressure in the cushion 212 is reached, missed or exceeded, whereas the initial internal pressure in the cushion 212 can be disregarded when the training device 210 is in an exercise mode and only an increase or decrease in the internal pressure in the cushion 212 as a result of the action of the user when performing the physical exercise is determined in order to generate the measurement signal 51 on this basis. The pumping mode or exercise mode of the training device 210 can be set, for example, by means of a user input into the evaluation apparatus 16, for example by means of a smartphone and an interface apparatus of the training device 210.

Figure 5:
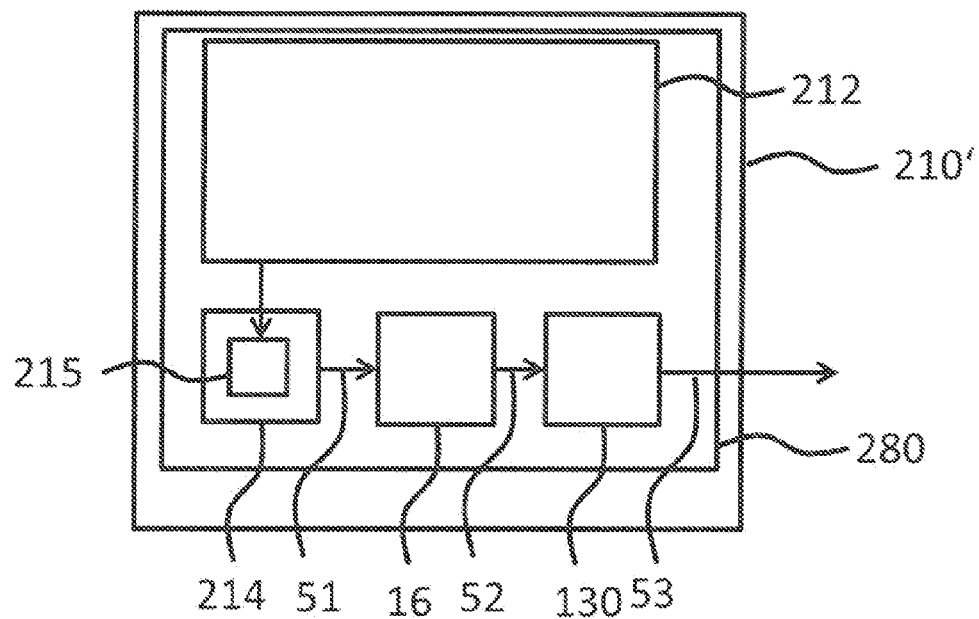
FIG. 5 is a schematic block diagram of a training device according to another further embodiment of the present invention.

FIG. 5 is a schematic block diagram of a training device 210' according to another further embodiment of the present invention. The training device 210' is a variant of the training device 210 and differs from the training device 210 in that the training device 210' is integrated in an exercise mat 280, as has previously been described in relation to the training device 110' and the exercise mat 180. The exercise mat 280 can in particular have the same features as the exercise mat 180 described above.

Figure 6:
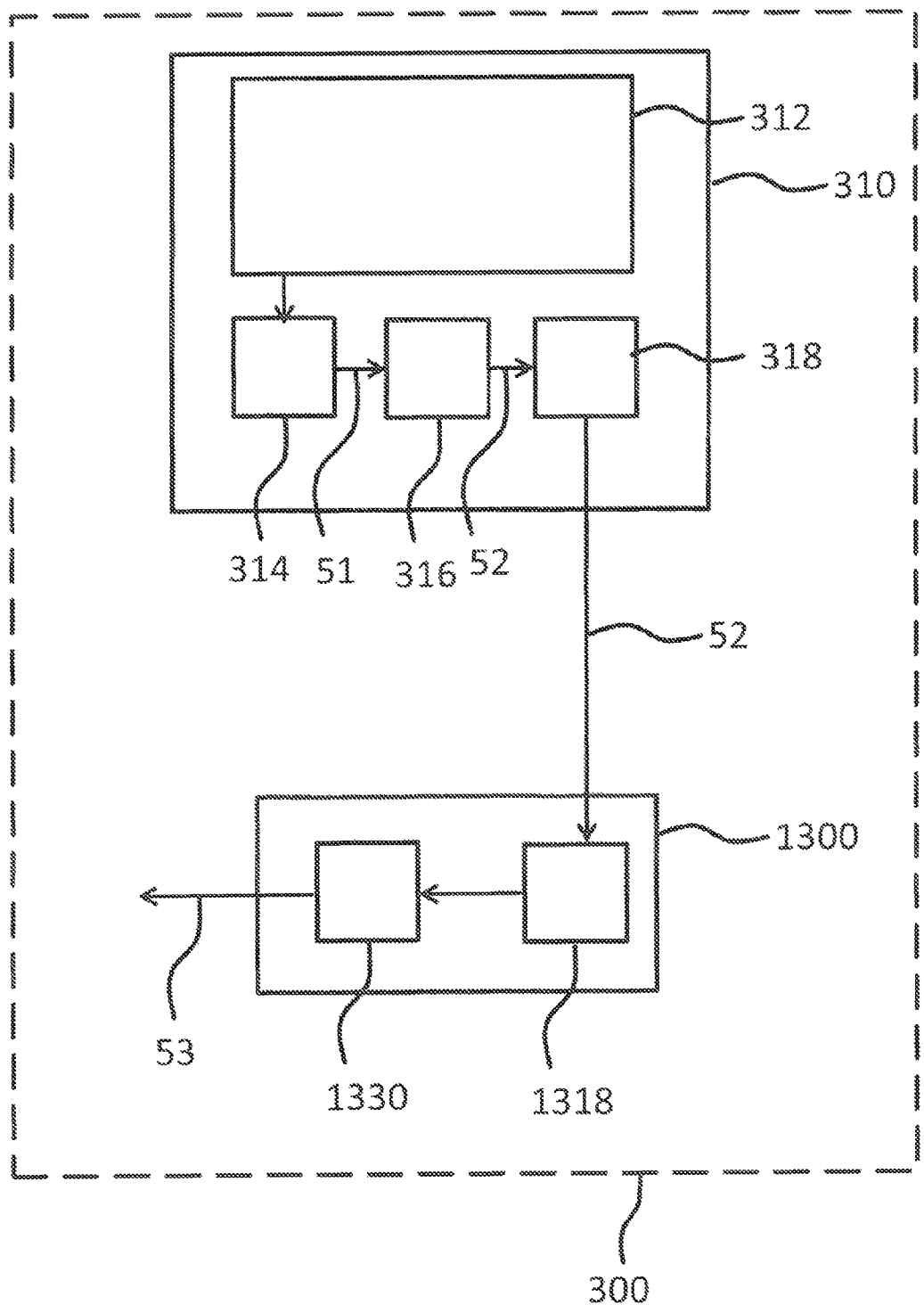
FIG. 6 is a schematic block diagram of a system for monitoring a physical exercise according to an embodiment of the present invention.

FIG. 6 is a schematic block diagram of a system 300 for monitoring a physical exercise according to an embodiment of the present invention. The system 300 comprises a training device 310 and an external terminal 1300, in other words a terminal separate from the training device 310. The training device 310 comprises a volume element 312, a sensor apparatus 314, an evaluation apparatus 316 and an interface apparatus 318. The volume element 312 and the sensor apparatus 314 can, for example, be formed like the volume element 112 and the sensor apparatus 114 or like the volume element 212 and the sensor apparatus 214. A combination of plastics material, in particular foam elements, and gas-filled, in particular air-filled, cushions is also conceivable.

As described above in relation to the training device 110' and the training device 210', the training device 310 can comprise an exercise mat 180, 280 or can be integrated in an exercise mat 180, 280 as a whole or in part.

Accordingly, the evaluation apparatus 316 is designed to generate the output signal 52 on the basis of the measurement signal 51 generated by the sensor apparatus 314. The output signal 52 is transmitted to the interface apparatus 318 of the training device 310. By means of the interface apparatus 318, the output signal 52 can be transmitted, in particular wirelessly, to a communication apparatus 1318 of the terminal 1300. For this purpose, in particular a wireless connection can be established between the interface apparatus 318 and the communication apparatus 1318, for example via Bluetooth, Zigbee, Ethernet, RFID or any other radio connection.

The terminal 1300 can in particular be a mobile terminal such as a smartphone or a tablet which executes an application, i.e. a program, configured accordingly.

The output signal 52 received by means of the communication apparatus 1318 is transmitted within the terminal 1300 to an output unit 1330. As described above in relation to the internal output apparatus 130, the output unit 1330 is designed to output an optical and/or acoustic and/or haptic information signal 53 to the user on the basis of the output signal 52. The output unit 1330 can, for example, comprise a display of a mobile terminal for outputting an optical information signal, a speaker of the mobile terminal for outputting an acoustic information signal 53 and/or a vibration unit of the mobile terminal for outputting a haptic information signal 53 to the user. The output unit 1330 can, for example, also comprise a pico projector. By means of the pico projector, a display can be projected onto a wall, a ceiling or another surface as an optical information signal 53 for example and the user can view this display without any aids when performing the exercise.

For example, a type of virtual numerical scale having a virtual needle can be displayed by means of the display and/or the pico projector of the mobile terminal 1300, the needle on the numerical scale always showing a current value for the force exerted on the volume element 312 by the user or the pressure exerted on the volume element 312. A value range which should advantageously be adhered to when performing the physical exercise can be highlighted on the virtual numerical scale. For example, as soon as the needle leaves the highlighted value range, an acoustic warning signal can be output, for example a sound or a voice response, which indicates to the user whether he has to increase or decrease the pressure exerted on the volume element 312 or the force exerted on the volume element 312 in order to move the needle back into the highlighted value range. A potentially disruptive acoustic output is thus only made to the user if the user needs to adjust his performance of the physical exercise.

Alternatively, only a for example uniform coloured area can also be output by the display or the pico projector, the colour or hue of which area indicates to the user whether the exerted force or the exerted pressure is within, below or above the value range. For example, a green light can be output when a pressure or a force is within the value range and a red light can be output when a pressure is above or below the value range. As a result, the need to adjust the manner in which the physical exercise is being performed can be displayed to the user even when said user cannot directly view the display on the mobile terminal 1300 since the uniform coloured area can, for example, be reflected into the user's eye by other objects.

The terminal 1300 can comprise an input apparatus, by means of which the user can adjust, in particular program, the evaluation apparatus 316 via the communication unit 1318 and the interface apparatus 318. For example, the user can input a physical exercise to be performed in an application on the terminal 1300, on the basis of which the evaluation apparatus 316 adjusts the value range with which the measurement signal 51 is compared. The user can, for example, also input personal data such as his weight, age, gender, etc. into the terminal 1300, and these data can be taken into account by the evaluation apparatus 316 when adjusting the value range.

If the volume element 312 and the sensor apparatus 314 are formed in the same manner as the volume element 212 and the sensor apparatus 214, as described above, and the training device 310 further comprises an optional filling apparatus which is designed to automatically apply an initial internal pressure to the cushion as the volume element 312, the initial internal pressure can be adjusted on the basis of inputs from the user into the terminal 1300. For example, the user can input his weight into the terminal 1300. A weight signal can be transmitted to the filling apparatus of the training device 310 by means of the communication unit 1318 via the interface apparatus 318 on the basis of the input weight. The filling apparatus can set the initial internal pressure on the basis of the weight signal. If, for example, the sensor apparatus 314 is designed to measure fluctuations in the internal pressure in a cushion as the volume element 312 in a particularly precise manner, which fluctuations fluctuate by a value of 5 bar, the initial internal pressure can be set automatically such that the internal pressure in the volume element 312, together with a pressure exerted on the volume element 312 by the weight of the user at the start of the physical exercise, is 5 bar.

Figure 7:
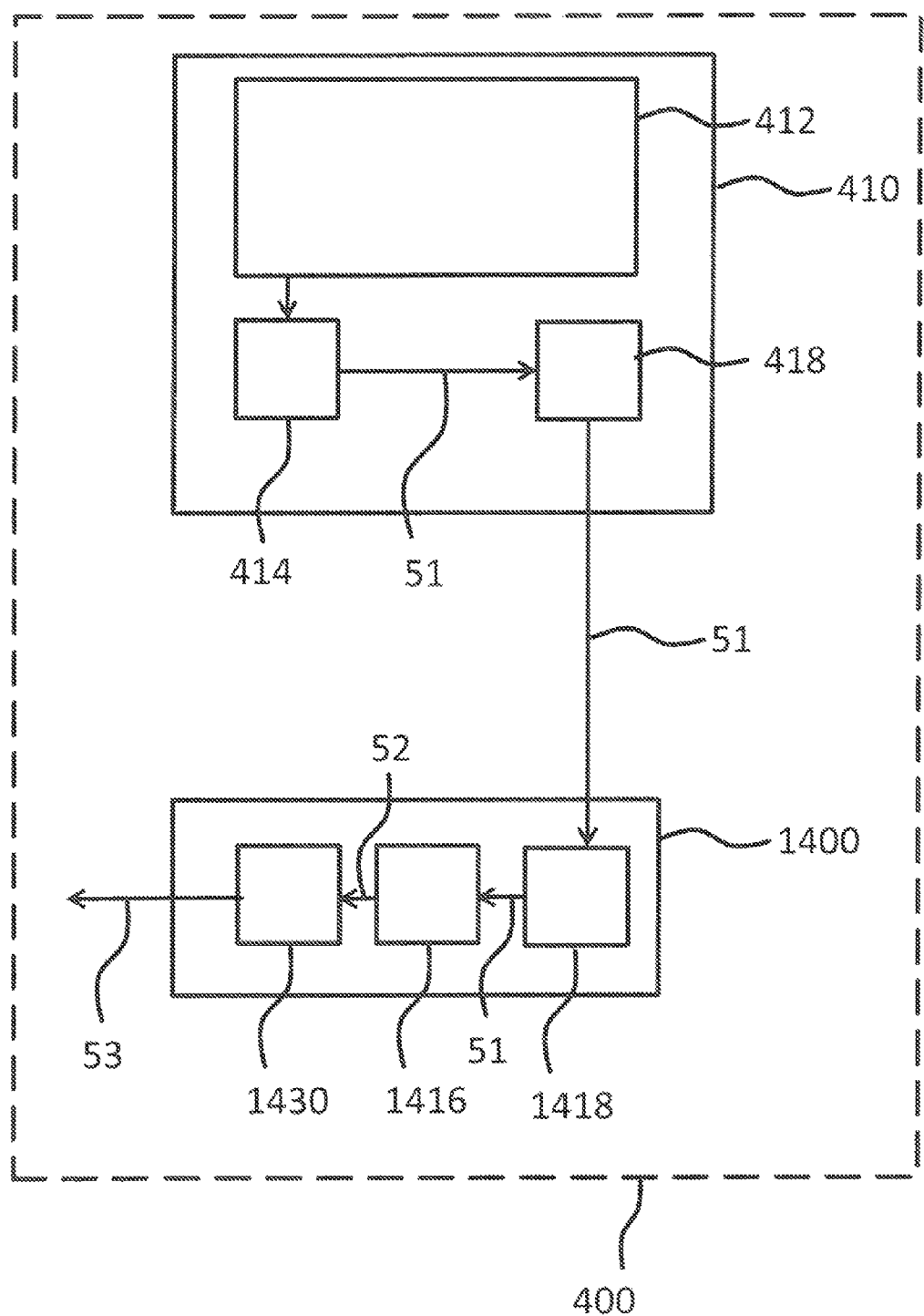
FIG. 7 is a schematic block diagram of a system for monitoring a physical exercise according to a further embodiment of the present invention.

FIG. 7 is a schematic block diagram of a system 400 for monitoring a physical exercise according to another further embodiment of the present invention. The system 400 comprises a training device 410 and an external terminal 1400, in other words a terminal 1400 separate from the training device 410. The training device 410 comprises a volume element 412, a sensor apparatus 414 and an interface apparatus 418. For example, the volume element 412 and the sensor apparatus 414 can be formed in the same way as the above-described volume elements 112, 212, 312 and the aforementioned sensor apparatuses 114, 214, 314.

As described above in relation to the training device 110' and the training device 210', the training device 410 can comprise an exercise mat 180, 280 or can be integrated as a whole or in part in an exercise mat 180, 280.

The interface apparatus 418 is designed to transmit the measurement signal 51 generated by the sensor apparatus 314 to a communication unit 418 of the terminal 1400 by means of the interface apparatus 418. The wireless communication between the interface apparatus 418 and the communication unit 1418 of the terminal 1400, which in particular can be a mobile terminal, can be formed in the same way as with the system 300, for example by means of Bluetooth. The terminal 1400 further comprises an evaluation unit 1416 which is designed to compare the measurement signal 51 received by the communication unit 1418 with a value range and/or a target value, and to automatically generate an output signal 52 on the basis of the result of the comparison, in particular as described above in relation to the evaluation apparatus 16, 116, 216, 316. The output signal 52 generated by means of the evaluation unit 1416 is transmitted to an output unit 1430, in particular of the terminal 1400, which can be formed as described above in relation to the output unit 1330.

A difference between the system 300 and the system 400 can be described in that, in the system 300, the measurement signal is evaluated in the training device 310 and the output signal 52 based thereon is transmitted to the terminal 1300, whereas, in the system 400, the evaluation unit 1416 arranged in the terminal 1400 generates the output signal 52 on the basis of the measurement signal 51 which is transmitted to the terminal 1400. In the system 400, therefore, the training device 410 can be designed in a technically simpler manner since an evaluation of the measurement signal 51, which in some cases can be technically complex, can take place in the terminal 1400.

The electric current requirement of the training device 410 can thus be reduced. The sensor apparatus 314 can, for example, also be supplied with the electrical energy required for generating the measurement signal 51 by means of electromagnetic waves emitted from the terminal 1400. In this case, the training device 410 does not need to be connected to an electrical mains supply or require an internal energy store, for example an accumulator or battery.

Figure 8:
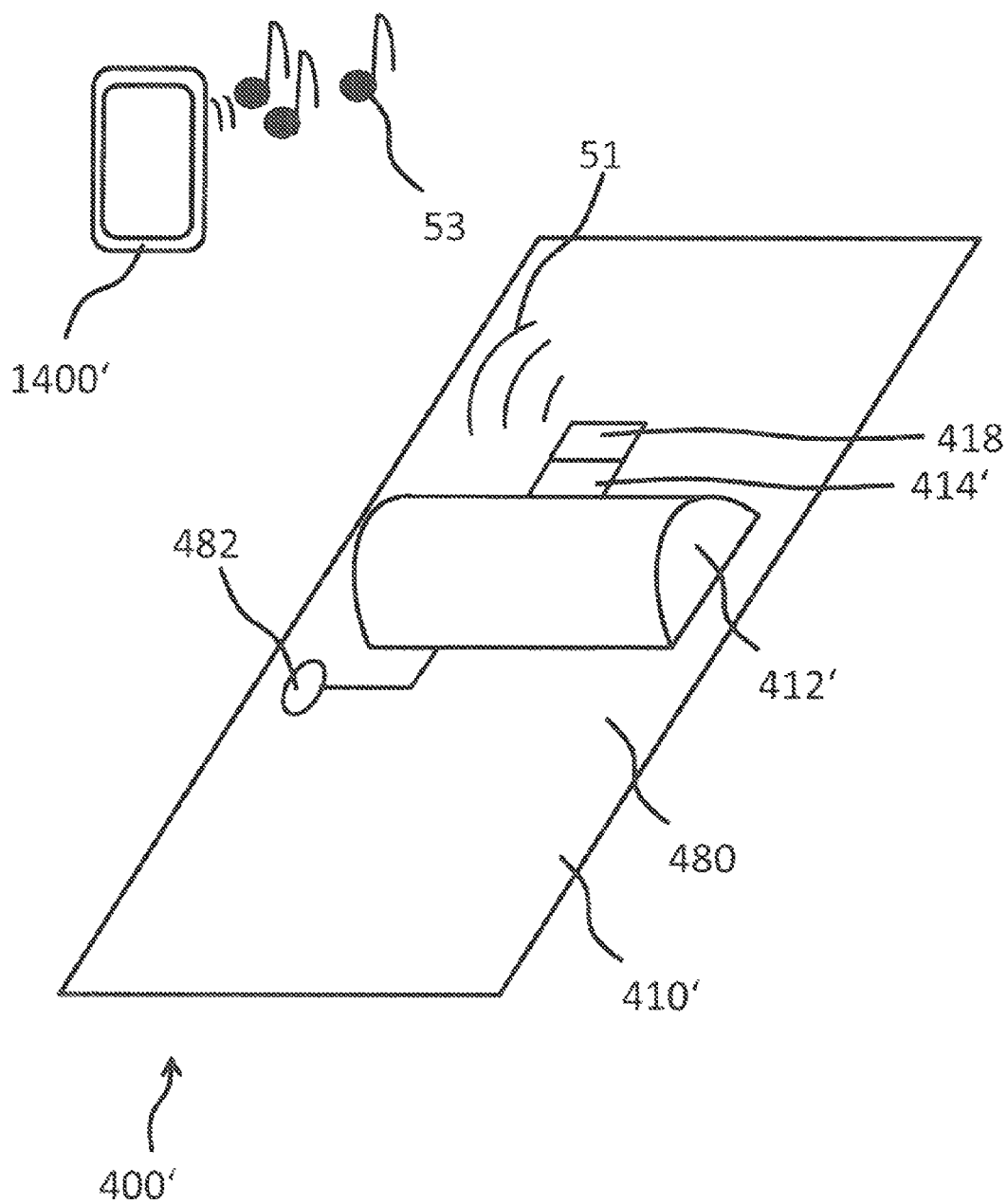
FIG. 8 is a schematic oblique view of a system for monitoring a physical exercise according to another further embodiment of the present invention.

FIG. 8 is a schematic oblique view of a system 400' for monitoring a physical exercise according to another further embodiment of the present invention. The system 400' is a variant of the system 400 according to FIG. 7. The training device 410' of the system 400' is integrated in an exercise mat 480, as described above in relation to the training device 110' and the exercise mat 180. The exercise mat 480 can have the same features as the aforementioned exercise mat 480.

The volume element 412' is formed as a cushion which can be pumped up, e.g. like the volume element 212. The training device 410' of the system 400' has a filling apparatus 482, by means of which the cushion 412' can be pumped up. The mobile terminal 1400' of the system 400' is in the form of a mobile telephone 1400', in particular a smartphone. The sensor apparatus 414' is formed in the same way as the sensor apparatus 214. The system 400' can be formed in the same way as the system 400 in all other respects. At least an acoustic information signal 53 in the form of sounds is output as the information signal by the mobile terminal 1400'.

Figure 9:
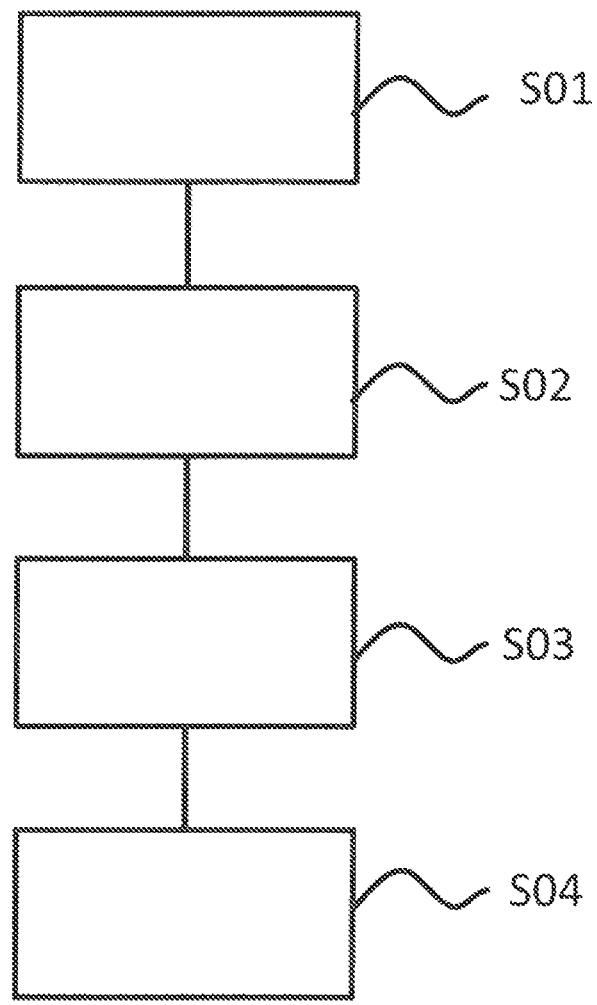
FIG. 9 is a schematic flow diagram to explain a method for monitoring a physical exercise according to another further embodiment of the present invention.

FIG. 9 is a schematic flow diagram for explaining a method for monitoring a physical exercise according to another further embodiment of the present invention. The method according to FIG. 9 can in particular be used with a training device 10; 110; 110'; 210; 210'; 310 according to the invention and/or a system 300; 400; 400' according to the invention of the present invention, and can also in particular be adjusted accordingly in terms of any development describing the training devices according to the invention and/or systems according to the invention.

In one step S01, a mechanical force and/or a pressure which a user exerts on a volume element 12; 112; 212; 312; 412; 412' while performing a physical exercise is detected. In a step S02, a measurement signal 51 is generated on the basis of the detected force and/or the detected pressure. In a step S03, an output signal 52 is generated on the basis of a comparison of the generated measurement signal 51 with a value range and/or a target value, for example by means of an evaluation apparatus 16; 116; 316 or an evaluation unit 1416.

In an optional step S04, an optical and/or acoustic and/or haptic information signal 53 is output on the basis of the output signal 52, for example by means of an output apparatus 130 or an output unit 1330; 1430.

Although the present invention has been described above on the basis of preferred embodiments, said invention is not limited thereto, but rather can be modified in many ways. In particular, the invention can be altered or modified in various ways without departing from the core of the invention.

For example, the output unit 1330; 1430 of the system 300; 400; 400' can also be separate from the mobile terminal 1300; 1400; 1400' instead of within the mobile terminal 1300; 1400; 1400'. The output unit 1330; 1430 can, for example, be within the training device 310; 410; 410' or separate from both the mobile terminal 1300; 1400; 1400' and the training device 310; 410; 410'. For example, the output unit 1330; 1430 can be a speaker coupled to the mobile terminal 1300; 1400 via Bluetooth.

The training device 110; 210; 310; 410 can in each case be formed having connection means such that it can be rigidly connected to a conventionally available exercise mat, for example by means of a hook and loop fastener, press studs, clasps or similar connection means.

Without further elaboration, it is believed that one skilled in the art can, using the preceding description, utilize the present invention to its fullest extent. The preceding preferred specific embodiments are, therefore, to be construed as merely illustrative, and not limitative of the remainder of the disclosure in any way whatsoever.

The preceding examples can be repeated with similar success by substituting the generically or specifically described reactants and/or operating conditions of this invention for those used in the preceding examples.

From the foregoing description, one skilled in the art can easily ascertain the essential characteristics of this invention and, without departing from the spirit and scope thereof, can make various changes and modifications of the invention to adapt it to various usages and conditions.

The entire disclosures of all applications, patents and publications, cited herein and of corresponding German Application No. 10 2015 214 394.5, filed Jul. 29, 2015 are incorporated by reference herein.

What is claimed is:

1. A training device for monitoring a physical exercise, comprising:
a volume element;
a sensor apparatus which is designed to detect a mechanical force or a pressure which a user exerts on the volume element while performing the physical exercise, and to generate a measurement signal on the basis of the detected force or the detected pressure;
an evaluation apparatus which is designed to compare the measurement signal generated by the sensor apparatus with a value range or a target value and to automatically generate an output signal on the basis of the result of the comparison; and
an internal output apparatus which is designed to automatically output an optical or acoustic or haptic information signal to the user on the basis of the generated output signal,
wherein the internal output apparatus is designed to adjust a wavelength of the optical information signal to be output or a frequency of the acoustic information signal to be output or a characteristic of the haptic information signal, on the basis of the output signal.

2. The training device according to claim 1,
wherein the sensor apparatus is designed to detect the mechanical force and/or the pressure continuously or at regular intervals and to generate the measurement signal based thereon continuously or at regular intervals; and
wherein the evaluation apparatus is designed to automatically adjust the generated output signal to the generated measurement signal, either continuously or at regular intervals.

3. The training device according to claim 1,
wherein the volume element is formed as a cushion which is filled with a gas or can be filled with a gas; and
wherein the sensor apparatus comprises a pressure sensor which is designed to detect an internal pressure in the cushion and to generate the measurement signal on the basis of the detected internal pressure.

4. The training device according to claim 1,
wherein the training device comprises an exercise mat in which at least the volume element and the sensor apparatus are integrated.

5. The training device according to claim 1, comprising an interface apparatus, by means of which the generated output signal can be transmitted to an external terminal which is designed to automatically output the optical or acoustic or haptic information signal to the user on the basis of the received output signal.

6. A system for monitoring a physical exercise, comprising:
a training device including
a volume element;
a sensor apparatus which is designed to detect a mechanical force or a pressure which a user exerts on the volume element while performing the physical exercise, and to generate a measurement signal on the basis of the detected force or the detected pressure; and an evaluation apparatus which is designed to compare the measurement signal generated by the sensor apparatus with a value range or a target value and to automatically generate an output signal on the basis of the result of the comparison, in which at least the volume element, the sensor apparatus, the evaluation apparatus and the interface apparatus are integrated; and a terminal which is separate from the training device and comprises an output unit which is designed to output an optical or acoustic or haptic information signal to the user on the basis of the output signal generated by the evaluation apparatus, wherein the output unit is designed to adjust a wavelength of the optical information signal to be output or a frequency of the acoustic information signal to be output or a characteristic of the haptic information signal on the basis of the output signal.

7. A system for monitoring a physical exercise, comprising:

a volume element;

a sensor apparatus which is designed to detect a mechanical force and/or a pressure which a user exerts on the volume element while performing the physical exercise, and to generate a measurement signal on the basis of the detected force and/or the detected pressure;

an interface apparatus, by means of which the generated measurement signal can be transmitted to a terminal; wherein the volume element, the sensor apparatus and the interface apparatus are integrated in a training device and wherein the terminal is separate from the training device; and the terminal which comprises an evaluation unit which is designed to compare the measurement signal generated by the sensor apparatus with a value range and/or a target value, to automatically generate an output signal on the basis of the result of the comparison and to transmit this signal to an output unit; and the output unit which is designed to output an optical and/or acoustic and/or haptic information signal to the user on the basis of the output signal generated by the evaluation unit.

8. A method for monitoring a physical exercise, comprising:

detecting a mechanical force or a pressure which a user exerts on a volume element while performing a physical exercise;

generating a measurement signal on the basis of the detected force or the detected pressure;

generating an output signal on the basis of a comparison of the generated measurement signal with a value range or a target value; and outputting an optical or acoustic or haptic information signal to the user on the basis of the generated output signal, wherein a wavelength of the optical information to be output or a frequency of the acoustic information signal to be output or a characteristic of the haptic information signal is adjusted on the basis of the output signal.

9. The system of claim 7, wherein the output unit is configured to adjust a wavelength of the optical information signal to be output or a frequency of the acoustic information signal to be output or a characteristic of the haptic information signal on the basis of the output signal.

* * * * *